United States Patent
Eshel

(10) Patent No.: US 7,018,398 B2
(45) Date of Patent: Mar. 28, 2006

(54) SYSTEM AND METHOD FOR TREATING URINARY TRACT DISORDERS

(75) Inventor: Uzi Eshel, Herzliya (IL)

(73) Assignee: Elmedical Ltd., Herzlia (IL)

( * ) Notice: Subject to any disclaimer, the term of this patent is extended or adjusted under 35 U.S.C. 154(b) by 298 days.

(21) Appl. No.: 10/389,948

(22) Filed: Mar. 18, 2003

(65) Prior Publication Data

US 2004/0186538 A1    Sep. 23, 2004

(51) Int. Cl.
*A61F 7/12* (2006.01)

(52) U.S. Cl. ............... 607/96; 607/104; 607/105; 607/138; 607/143; 606/27; 606/191; 606/192; 606/193; 600/29; 600/31

(58) Field of Classification Search .......... 607/88–110, 607/138, 143; 606/10–25, 27; 600/29, 31, 600/101, 191–198; 604/96.01, 113
See application file for complete search history.

(56) References Cited

U.S. PATENT DOCUMENTS

| | | | | |
|---|---|---|---|---|
| 5,257,977 A | * | 11/1993 | Eshel | 604/113 |
| 5,263,931 A | * | 11/1993 | Miller | 604/103.13 |
| 5,480,417 A | * | 1/1996 | Hascoet et al. | 607/101 |
| 5,509,929 A | * | 4/1996 | Hascoet et al. | 607/101 |
| 5,545,161 A | * | 8/1996 | Imran | 606/41 |
| 5,549,559 A | * | 8/1996 | Eshel | 604/113 |
| 5,620,480 A | * | 4/1997 | Rudie | 607/101 |
| 5,643,335 A | * | 7/1997 | Reid et al. | 607/101 |
| 5,755,754 A | * | 5/1998 | Rudie et al. | 607/101 |
| 5,916,195 A | * | 6/1999 | Eshel et al. | 604/96.01 |
| 6,102,929 A | * | 8/2000 | Conway et al. | 606/192 |
| 6,440,127 B1 | * | 8/2002 | McGovern et al. | 606/41 |
| 6,743,226 B1 | * | 6/2004 | Cosman et al. | 606/41 |
| 6,849,063 B1 | * | 2/2005 | Eshel et al. | 604/113 |

* cited by examiner

Primary Examiner—A. Farah

(57) ABSTRACT

A method, device, and system for treatment of urinary tract disorders is provided. The device includes a catheter having multiple lumens for insertion into a urinary bladder and for providing fluid flow within the bladder and within the fluid reservoir within the urethra. The device further includes an anchor to be placed within the bladder. A port hub having multiple ports is connected at a proximal end of the catheter. A method of treatment includes providing heated fluid to a urinary bladder and to a fluid reservoir for insertion into an adjacent organ such as the urethra. Simultaneous treatment or separate treatment may be done. Optionally, a medicated solution may be added to the heated fluid. Additionally, pressure may be adjusted so as to optimize the therapeutic effect.

16 Claims, 7 Drawing Sheets

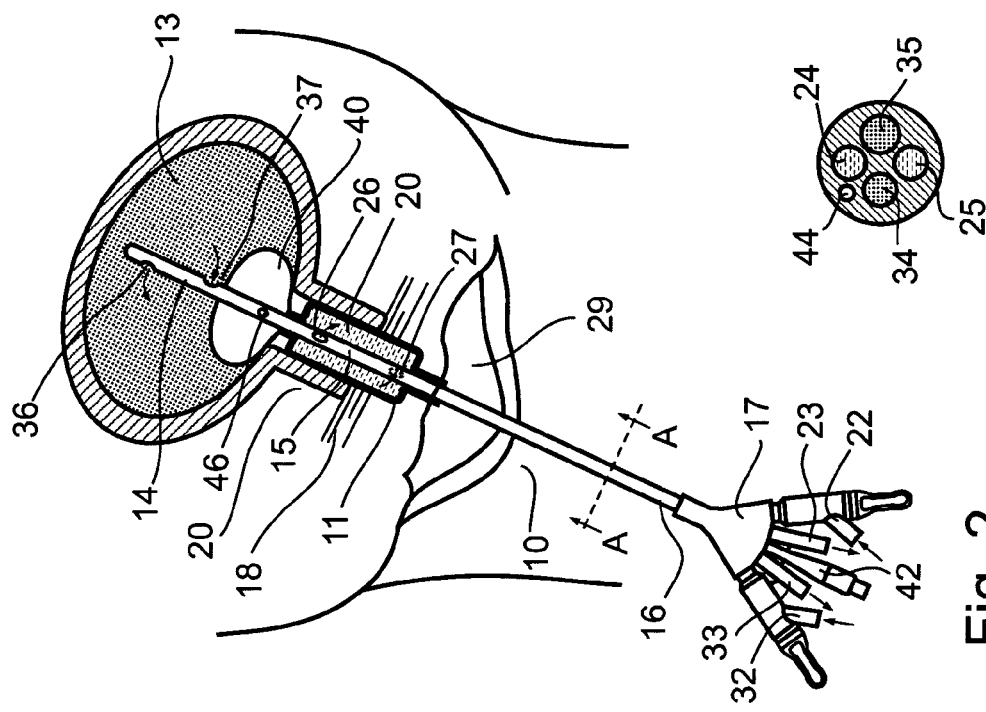
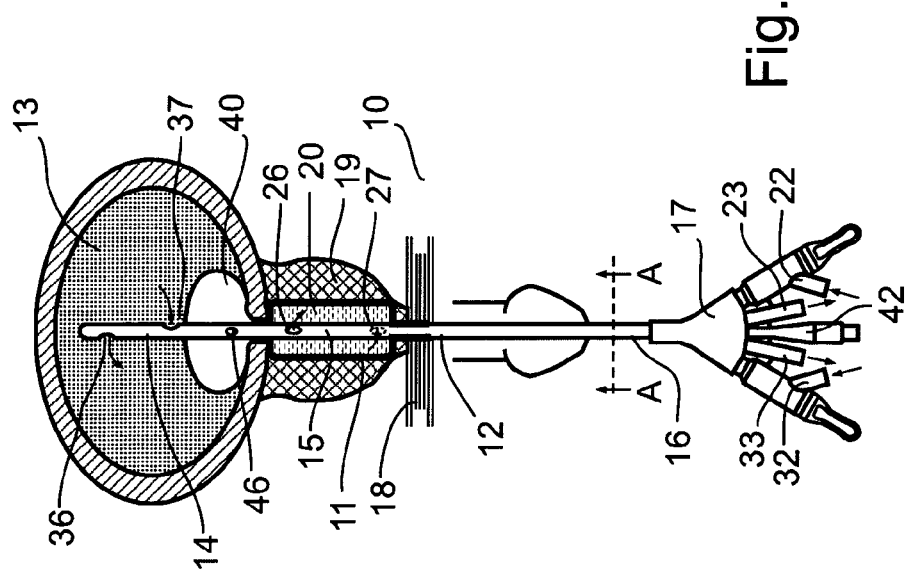

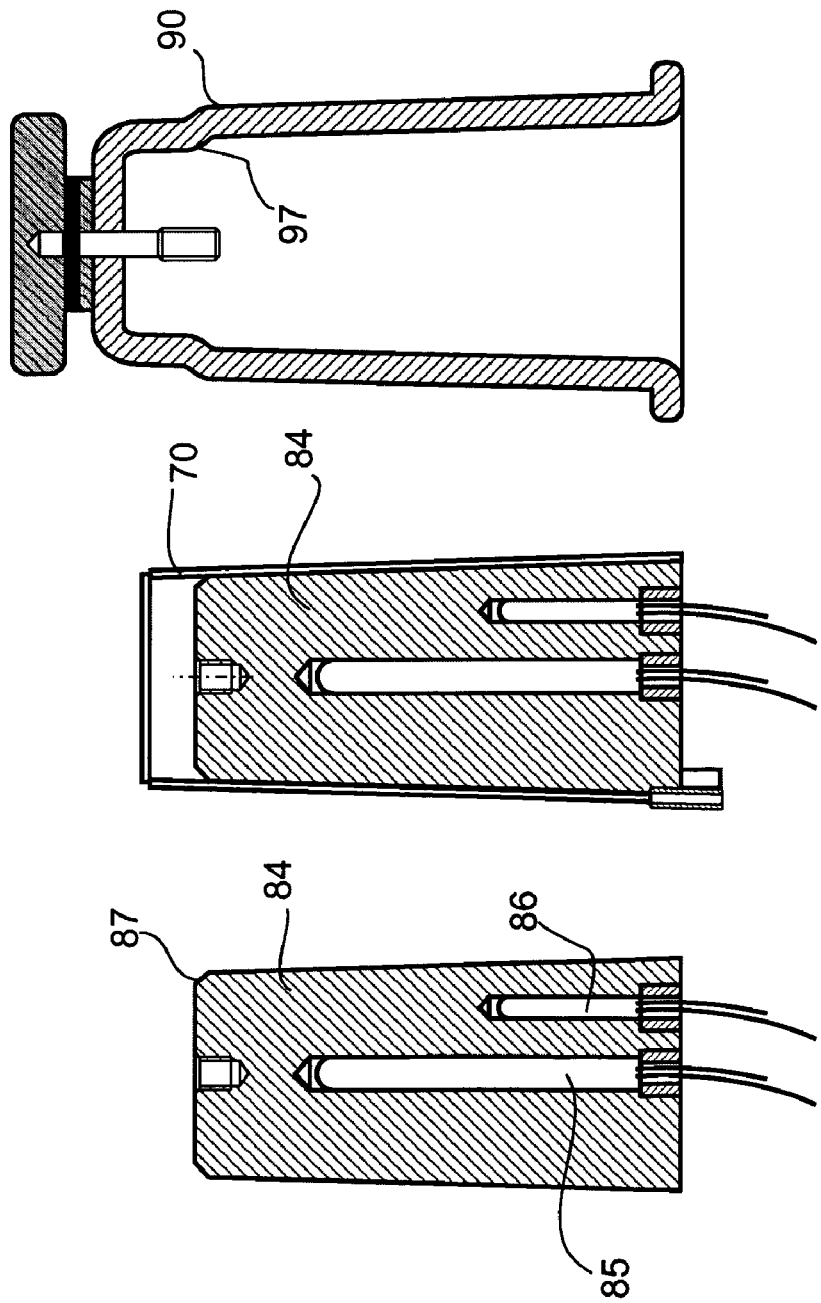

SYSTEM AND METHOD FOR TREATING URINARY TRACT DISORDERS

FIELD AND BACKGROUND OF THE INVENTION

The present invention relates to a system and method for treatment of urinary tract disorders and, more particularly, to a device and method for insertion into a urethra and/or bladder that is capable of simultaneously delivering moderate heat, pressure, and/or drugs to provide relief in the pelvic area.

There is a wide array of urinary tract inflammatory disorders, which can generally be broken down into two categories: bacterial and non-bacterial. Bacterial inflammatory disorders are relatively easy to diagnose and treat. Non-bacterial inflammatory disorders are generally less understood, harder to diagnose, and harder to treat successfully. Symptoms usually include pelvic pain or discomfort, urinary urge or frequency, bladder pain, and even pain in neighboring parts of the body such as the abdomen, lower back or thighs. Patients presenting with such symptoms for whom bacterial causes have been ruled out may be diagnosed with one of the non-bacterial disorders. For example, a male disorder called chronic pelvic pain syndrome (CPPS), also known as chronic non-bacterial prostatitis, manifests itself in men as general pain or discomfort in the urethra, perineum, bladder area, penis, testicles, or general pelvic area. Similar symptoms typify another condition occurring mainly in women called interstitial cystitis (female to male ratio approximately 9:1), which is characterized by a non-bacterial chronic inflammatory condition of the bladder or bladder epithelium permeability to toxic agents from the urine.

Both CPPS and interstitial cystitis, which may be related to one another epidemiologically, are treated symptomatically. It should also be noted that it is possible that many men who were diagnosed as CPPS sufferers in reality had interstitial cystitis, and thus, similar treatment may be warranted for both of these conditions. Treatment methods include oral drug therapy, bladder hydrodistension, bladder drug instillation, massage therapy, laser treatments, biofeedback, diet, and even surgery. While some of these methods are partially successful, often the symptoms are not fully alleviated or return shortly after treatment. There are also urinary tract sensory disorders such as overactive bladder or detrusor-sphincter dyssynergia, both of which may be manifested in the urethra and the bladder. Current drug therapies are insufficient, and thus, there is a need for new treatments and treatment methods.

It has been recognized by physicians that applying heat to the prostate may be helpful in easing some of the symptoms associated with CPPS. Heat therapy has been administered in the form of transrectal microwave hyperthermia (temperatures between 41 and 45 degrees Celsius), transurethral microwave hyperthermia, transurethral hot balloon therapy, and transurethral microwave thermotherapy (temperatures over 46 degrees Celsius that cause tissue ablation to exposed tissue).

Hyperthermia treatments have certain advantages, particularly when used in combination with drugs. For example, hyperthermia has been shown to alter intracellular distribution of drugs, while increasing both their metabolism and reaction rates. Hyperthermia provides additional benefits in treatment of cancer, such as transitional cell carcinoma (TCC), or superficial bladder cancer, since it has been shown to increase drug uptake by neoplastic cells while at the same time inhibiting DNA repair in damaged neoplastic cells. However, hyperthermia alone does not necessarily provide long-lasting therapeutic effects because of a lack of sufficient heat supplied by current hyperthermia devices.

It has been shown that heat therapies at higher temperatures, such as transurethral microwave thermotherapy, have better clinical results over the long term, particularly for CPPS. The reason for the beneficial effect is largely unknown, but it has been hypothesized that the higher level of heat in the surrounding non-ablated tissue either improves blood supply or shortens the inflammatory process.

The disadvantage of thermotherapy is that due to the high temperatures near the applicator, a cooling system must be used to protect the urethra while heating the prostate, for example, rendering any system for delivery of thermotherapy relatively bulky and expensive. Additionally, there is a risk of damage to surrounding organs as well as to the prostate itself. Furthermore, microwave heat therapy in particular is problematic in that the radiative energy, which transforms into heat within the tissue, is difficult to control and hard to predict in terms of temperature. Additionally, when hyperthermia is combined with drug treatments, it is essential to avoid excessively high temperatures in order to avoid damage to the drug and its effect on the tissue.

There is thus a widely recognized need for, and it would be highly advantageous to have, a device and method for treatment of CPPS and/or interstitial cystitis for delivery of hyperthermia therapy which is devoid of the above limitations.

SUMMARY OF THE INVENTION

According to a preferred embodiment of the present invention, there is provided a catheter for treating urinary tract disorders. The catheter includes: (a) a catheter body being sized and configured such that when placed within the urinary tract of an individual a proximal portion of the catheter body resides outside the body of the individual, a middle portion of the catheter body resides within a urethra of the individual and a distal portion of the catheter body resides within a urinary bladder of the individual; (b) a fluid reservoir being attached to the catheter body at the middle portion of the catheter body; (c) a first conduit including at least one lumen, the first conduit being for communicating reservoir fluid from a first source outside the body through the proximal portion of the catheter body to the fluid reservoir; and (d) a second conduit including at least one lumen, the second conduit being for communicating bladder fluid from a second source outside the body through the catheter body and into the urinary bladder; wherein the fluid, when heated and provided within the fluid reservoir and/or the urinary bladder enables treatment of urinary tract disorders.

According to yet another aspect of the present invention, there is provided a method of treating a urinary tract disorder in an individual. The method includes simultaneously heating urethral and urinary bladder tissue of the individual for a predetermined time period thereby treating the urinary tract disorder in the individual.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is an illustration of a device as used in a male, in accordance with one embodiment of the present invention;

FIG. 2 is an illustration of the device of FIG. 1 as used in a female, in accordance with one embodiment of the present invention;

FIG. 3 is a cross-sectional view of a catheter from the system of FIG. 1 and FIG. 2;

FIG. 10 is a cross-section illustration of a heating element in accordance with one embodiment of the present invention;

FIG. 11 is a cross-section illustration of the heat exchanger bag of FIG. 9 placed on top of the heating element of FIG. 10;

FIG. 12 is a cross-section of a cover;

DESCRIPTION OF THE PREFERRED EMBODIMENTS

Figure 6:
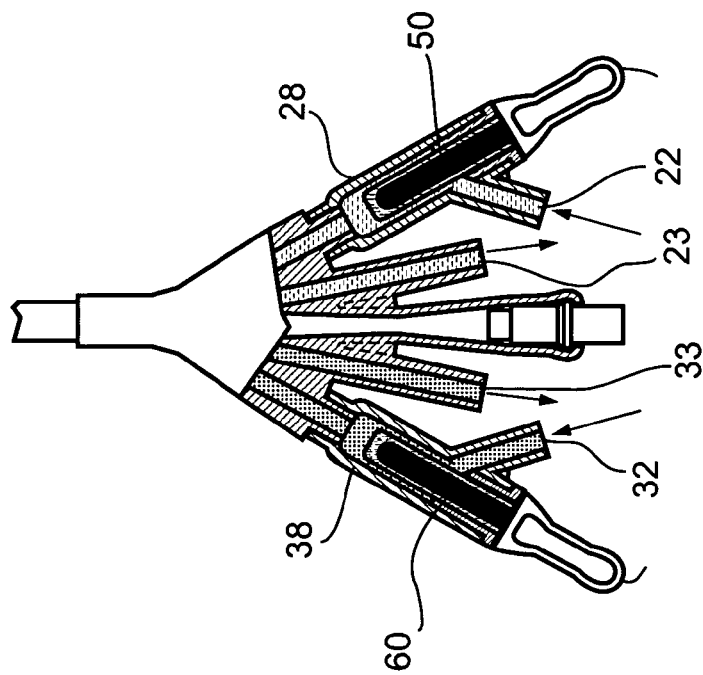
FIG. 6 is a cross-sectional view of a port hub of FIG. 4 with the temperature sensors of FIG. 5 placed therein.

The present invention is of a device and method for treating urinary tract disorders. Specifically, the present invention can be used to improve hyperthermia treatment of symptoms of a urinary tract condition, such as CPPS or interstitial cystitis, by increasing heat circulation in the pelvic area while not subjecting any organs to a potentially damaging level of heat.

Prior art devices either lack sufficient heat circulation to provide any long-term benefits, or are configured to deliver treatment at relatively high temperatures. Those that use high temperatures either potentially cause damage to surrounding tissue or these effects must be counteracted with a cooling device.

An example of a prior art device for thermal treatment is disclosed in U.S. Pat. No. 5,257,977 to Eshel. The device described therein is an insulated catheter for insertion into a narrow body orifice such as the urethra. It is used to provide heated fluid under pressure to the urethra or the bladder. Although it is suitable for hyperthermia treatment as well as ablative heat treatment, the heat applied to the treated tissue by hyperthermia treatment is not sufficient so as to provide long-term benefit.

Another example of a prior art device for thermal treatment is disclosed in U.S. Reissued Pat. No. 37,315 to Lev. The device described therein is designed for hyperthermia therapy of tumors by means of microwave radiation. It includes a catheter with a sheathed radiofrequency antenna, surrounded by a flow of liquid and an inflatable balloon. The catheter is introduced into the bladder through the urethra. The liquid, which optionally includes a cytotoxic substance, is circulated through the bladder while the bladder is then heated through.

Disadvantages of hyperthermia treatments such as the ones described are that insufficient temperatures are used to provide long-lasting therapeutic effects. Particularly with respect to radiative energy, which is difficult to control, temperatures are generally kept on the low-end, to avoid tissue damage by undetected, higher than monitored temperatures. The use of these low-end temperatures may provide inferior results.

The present invention seeks to overcome the disadvantages of the prior art by providing either simultaneous or sequential heat treatment to more than one organ within the urinary tract. By providing simultaneous hyperthermia treatment of the urethra or prostate and the bladder, better clinical outcomes can be achieved, even without additional therapy such as drugs, pressure or radiation. The rationale for this type of treatment is that more conductive heat can be provided to the region as a whole without the need for an increase in temperature to the ablative level. Furthermore, since the diagnosis of some urinary tract disorders is not always clear, and due to the overlapping nature of diseases such as CPPS and interstitial cystitis, and the involvement of both the bladder and urethra in detrusor-sphincter dyssynergia, treatment of more than one organ may be helpful since the disease might be originating from both or either location.

The principles and operation of a device and method according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Thus, according to one aspect of the present invention there is provided a catheter for treating urinary tract disorders in an individual. As is further described hereinunder, the catheter of the present invention is designed and configured so as to allow simultaneous heating of both the urethra and bladder of the individual thus providing substantial treatment benefits to individuals suffering from urinary tract disorders such as CPPS, interstitial cystitis, detrusor-sphincter dyssynergia, overactive bladder, and superficial bladder cancer (TCC).

Reference is now made to FIG. 1, which is a cross-section illustration of a device 10 in accordance with one embodiment of the present invention. Device 10 includes a catheter 12 having a distal portion 14, a middle portion 15, and a proximal portion 16, and a fluid port hub 17 at proximal portion 16 of catheter 12. Distal portion 14 of catheter 12 is designed to be inserted into a urinary bladder 13, and includes a bladder inlet opening 36 and a bladder outlet opening 37 for fluid flow within urinary bladder 13, and an anchor 40 for holding catheter 12 in place and for preventing outward migration of device 10 once it is situated in the body. An anchor opening 46 allows for fluid flow into and out of anchor 40. In a preferred embodiment, anchor 40 is an inflatable balloon, which can be inserted into urinary bladder 13 while deflated and can subsequently be inflated so as to anchor catheter 12 into place. In alternative embodiments, anchor 40 is of another configuration, such as a malecot. Middle portion 15 of catheter 12 includes a fluid reservoir 20 with a reservoir inlet opening 26 and a reservoir outlet opening 27, for fluid flow within fluid reservoir 20. In a preferred embodiment, fluid reservoir 20 is an inflatable balloon. In alternative embodiments, fluid reservoir 20 is a bladder or a membrane. In one embodiment, fluid reservoir 20 is comprised of permeable or semi-permeable material to allow diffusion of particles, including drugs or medicaments.

Middle portion 15 of catheter 12 is designed to be inserted into a urethra. FIG. 1 depicts catheter 12 as located with respect to male anatomy, while FIG. 2 depicts catheter 12 with respect to female anatomy. As shown in FIG. 1 for a male, fluid reservoir 20 of middle portion 15 is positioned within the urethra 11, which is within a prostate 19. In one embodiment, fluid reservoir 20 extends into and beyond the external sphincter 18. As shown in FIG. 2 for a female, fluid reservoir 20 of middle portion 15 is positioned within urethra 11, and extends through the sphincter 18. In one embodiment, fluid reservoir 20 extends past urethra 11 and through the area of the female genitalia 29. It should be readily understood that fluid reservoir 20 of middle portion 15 of catheter 12 is designed to be used throughout the region of the urinary tract, and is not limited to any specific organ or segment thereof.

At proximal portion 16 of catheter 12, fluid port hub 17 includes a series of ports for fluid movement within catheter 12. In a preferred embodiment, the following ports are included in fluid port hub 17: reservoir inlet port 22; reservoir outlet port 23; bladder inlet port 32; bladder outlet port 33; and anchor port 42. Each port is connected to a corresponding lumen or conduit within catheter 12, as shown in a cross-sectional view along section A-A of catheter 12 depicted in FIG. 3. Thus, reservoir inlet port 22 is connected to reservoir inlet lumen 24; reservoir outlet port 23 is connected to reservoir outlet lumen 25; bladder inlet port 32 is connected to bladder inlet lumen 34; bladder outlet port 33 is connected to bladder outlet lumen 35; and anchor port 42 is connected to anchor lumen 44. These lumens, in turn, are connected to openings in various locations on catheter 12, as follows. Reservoir inlet lumen 24 is connected to reservoir inlet opening 26; reservoir outlet lumen 25 is connected to reservoir outlet opening 27; bladder inlet lumen 34 is connected to bladder inlet opening 36; bladder outlet lumen 35 is connected to bladder outlet opening 37; and anchor lumen 44 is connected to anchor opening 46. In alternative embodiments, more or fewer ports and lumens may be used.

Fluid circulates throughout device 10, both freely within urinary bladder 13, and within fluid reservoir 20, providing pressure, heat, medication or a combination thereof to the various areas within the urinary tract. Reservoir inlet port 22 provides fluid through reservoir inlet lumen 24 and out through reservoir inlet opening 26 into fluid reservoir 20, thereby expanding fluid reservoir 20 within urethra 11. Fluid from fluid reservoir 20 exits through reservoir outlet opening 27, and returns through reservoir outlet lumen 25 within catheter 12 and reservoir outlet port 23. In one embodiment, the fluid flowing into and out of fluid reservoir 20 is a gas. In a preferred embodiment, the fluid flowing into and out of fluid reservoir 20 is a liquid, such as water or saline solution, and may further include drugs. Bladder inlet port 32 provides fluid flow through bladder inlet lumen 34 and bladder inlet opening 36 into urinary bladder 13. Fluid circulates through urinary bladder 13 and returns via bladder outlet opening 37 through bladder outlet lumen 35 and exits through bladder outlet port 33. In one embodiment, the fluid flowing into and out of the bladder is a sterile liquid, such as water. In a preferred embodiment, the fluid flowing into and out of the bladder is a sterile liquid, such a saline solution. In an exemplary preferred embodiment, the fluid flowing into and out of the bladder is an augmented sterile liquid, such as sterile water augmented with medication, as will be described in further detail hereinbelow. Anchor port 42 provides fluid through anchor lumen 44 via anchor opening 46 into anchor 40, thereby expanding anchor 40 so as to hold catheter 12 in place. Thus, anchor 40 is meant to stay inflated throughout a procedure using device 10, and once the procedure is completed, the fluid is removed via anchor opening 46 through anchor lumen 44 and anchor port 42. Since fluid does not circulate throughout the procedure, only one lumen is needed.

Figure 5:
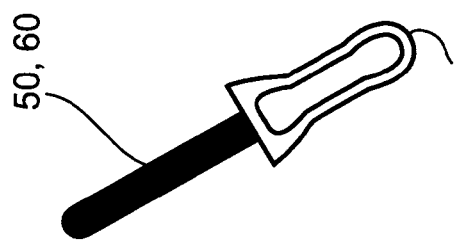
FIG. 5 is a view of a temperature sensor, which is insertable into the port hub of FIG. 4.
Figure 4:
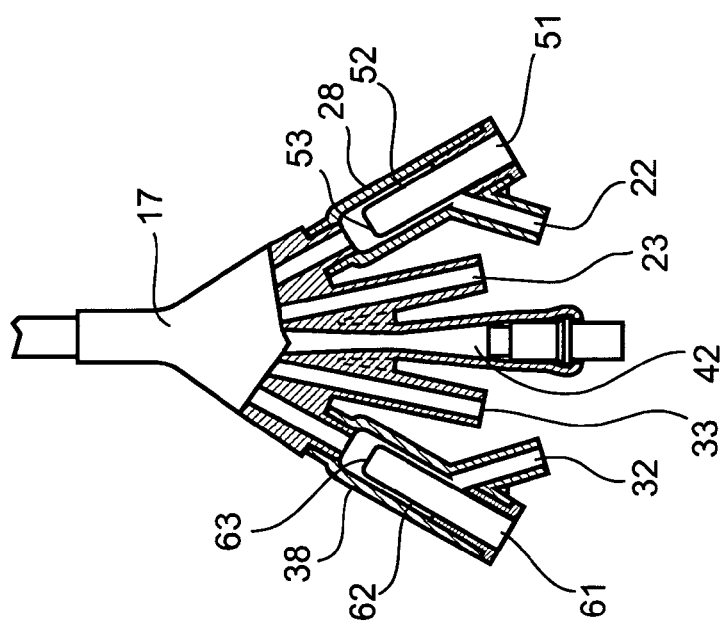
FIG. 4 is a cross-sectional view of a port hub of the device of FIG. 1 and FIG. 2.

Reference is now made to FIGS. 4–6, which illustrate a cross-sectional view of fluid port hub 17 with and without temperature sensors 50, 60 inside reservoir inlet housing 28 and bladder inlet housing 38, respectively. FIG. 4 illustrates fluid port hub 17 without temperature sensors 50, 60; FIG. 5 is an illustration of a temperature sensor 50 or 60, according to an embodiment of the present invention; and FIG. 6 illustrates fluid port hub 17 with temperature sensors 50, 60 placed therein. According to alternative embodiments, only one, or neither of the ports have a temperature sensor 50 or 60 located therein.

As shown in FIG. 4, reservoir inlet port 22 is designed within reservoir inlet housing 28 and bladder inlet port 32 is designed within bladder inlet housing 38. Housings 28, 38 include temperature sensor membranes 52, 62, respectively. For purpose of discussion, only reservoir inlet housing 28, with temperature sensor membrane 52 and reservoir inlet port 22 will be described in detail, but it will be readily understood that bladder inlet housing 38, temperature sensor membrane 62 and bladder inlet port 32 have a similar or identical configuration. Temperature sensor membrane 52 is comprised of an elastic material, such as silicon, PVC, polyurethane or any other suitable material. Membranes 52, 62 have tips 53, 63 and entrances 51, 61 to receive temperature sensors 50, 60. Reservoir inlet port 22 is configured for introduction of fluid into reservoir inlet lumen 24. Fluid introduced therein surrounds temperature sensor membrane 52 while being introduced into reservoir inlet lumen 24.

When temperature sensor 50 is placed into reservoir inlet housing 28 through entrance 51, tip 53 of temperature sensor membrane 52 is configured to extend inwards, thereby elongating membrane 52 so as to provide a snug fit of temperature sensor 50 within temperature sensor membrane 52, as seen in FIG. 6. In a preferred embodiment, temperature sensor 50 is cone-shaped, enabling ease of entry almost fully into reservoir inlet housing 28, followed by a close fit due to the deformation of temperature sensor membrane 52.

Temperature sensors 50, 60 are fabricated from a metal such as stainless steel, within which is placed a temperature sensing device such as a thermocouple junction, thermistor, or PT 100 device.

Temperature sensors 50, 60 are designed to measure the temperature of the fluid inserted into fluid reservoir 20 and/or urinary bladder 13. In this way, the temperature of fluid flowing through device 10 can be monitored and adjusted. In one embodiment, the optimal temperature is 41–46 degrees Celsius. In a preferred embodiment, the optimal temperature is 44 degrees Celsius. In alternative embodiments, temperature sensors 50, 60 are located within fluid reservoir 20 or inside distal portion 14 or within the urinary bladder 13.

Figure 7:
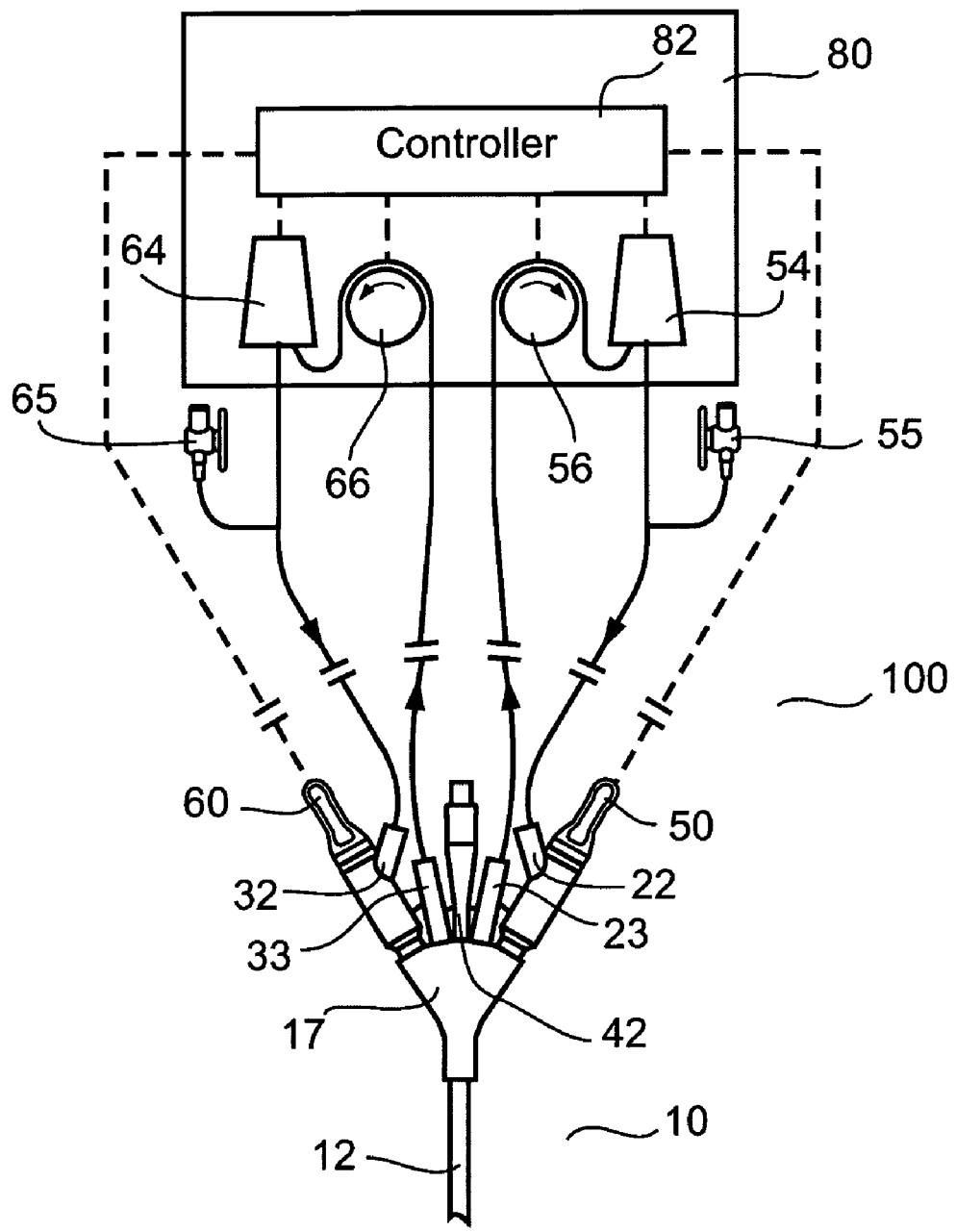
FIG. 7 is an illustration of a heating system, in accordance with one embodiment of the present invention.

Reference is now made to FIG. 7, which is an illustration of a urinary tract treatment system 100 including a heating device 80, in accordance with one embodiment of the present invention. Heating device 80 is connected to port hub 17 via several fluid connections using tubing (shown in FIG. 7 as solid lines) and electrical connections using wire (shown in FIG. 7 as dotted lines), and includes a controller 82, a set of peristaltic pumps 56, 66, and a set of fluid heating systems 54, 64. Electrical connections are present between controller 82 and temperature sensors 50, 60, peristaltic pumps 56, 66, and fluid heating systems 54, 64. Heating device 80, located outside the body, administers and controls heat and pressure to the fluid flowing throughout device 10. Two heating loops are formed, on each side of heating device 80. One loop heats fluid which has returned from fluid reservoir 20 before sending it back into fluid reservoir 20, and the other loop heats fluid which has returned from urinary bladder 13 before sending it back into urinary bladder 13. Thus, in both locations, newly heated fluid consistently replaces cooled fluid returning from inside device 10. The loops can continue for as long as the user desires.

Referring first to the heating loop for fluid reservoir 20, fluid coming from reservoir outlet port 23 flows into heating device 80. Within heating device 80, it flows through a peristaltic pump 56, and through a fluid heating system 54. Fluid then flows out of heating device 80 and into reservoir inlet port 22. Temperature sensor 50 measures the incoming fluid and sends feedback to controller 82, allowing the temperature to be adjusted for the subsequent stream of fluid. Temperatures are closely monitored and controlled by controller 82. Fluid enters (and exits) urinary tract treatment system 100 via filling ports 55, 65. Filling ports 55, 65 are also used to adjust pressure or provide alternating pressures within each loop of system 100. This can be accomplished, for example, by placing a column of fluid over system 100 wherein the column is connected to filling port 55 or 65, and thereafter changing the height of the column. At the end of treatment, fluid is removed from both loops of system 100 through filling ports 55, 65.

Similarly for the second heating loop for urinary bladder 13, fluid coming from bladder outlet port 33 flows into heating device 80. Within heating device 80, it flows through a peristaltic pump 66, and through a fluid heating system 64. Fluid then flows out of heating device 80 and into bladder inlet port 32. Temperature sensor 60 measures the incoming fluid temperature and sends feedback to controller 82, allowing the temperature to be adjusted for the subsequent stream of fluid. Temperatures are closely monitored and controlled by controller 82.

Peristaltic pumps 56, 66 can be any pump known in the art, such as Masterflex L/S catalog number TH-77910-20 from Cole-Parmer Instrument Company (Vernon Hills, Ill., USA), or 313 FAC/D OEM pump from Watson-Marlow Bredel Pumps (Wilmington, Mass., USA). Controller 82 can be any suitable controller, such as a standard PC board, or ATR 110 Controller Single Setpoint or ATR 240 Controller Double Setpoint from Pixsys (Padua, Italy). Fluid heating systems 54, 64 will be described in greater detail hereinbelow.

Figure 8:
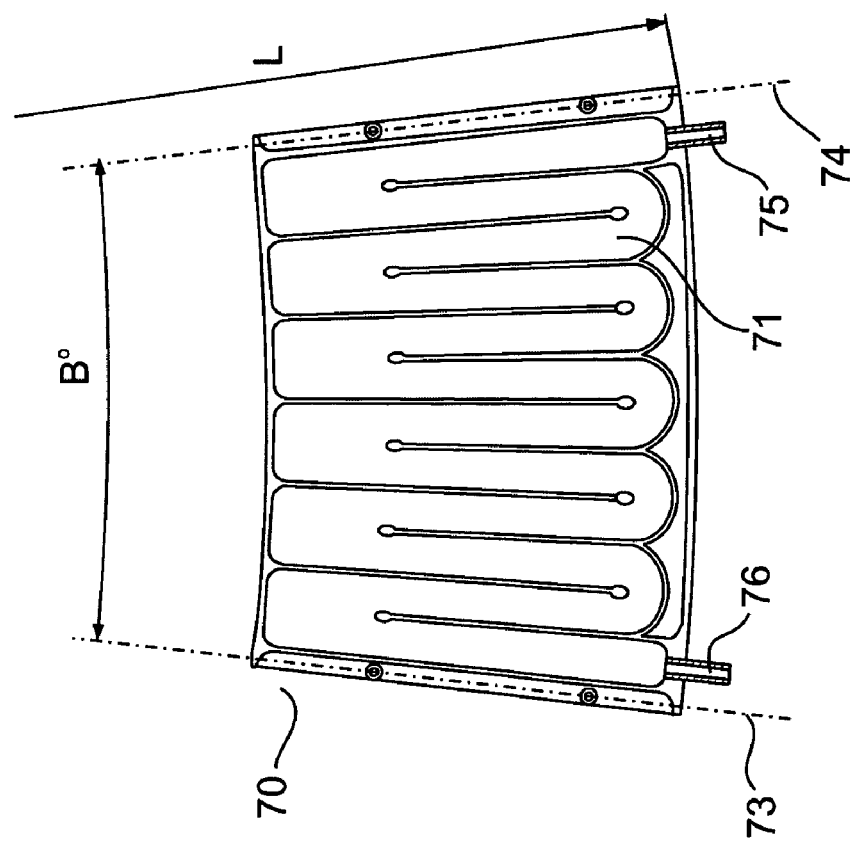
FIG. 8 is a flat view of a heat exchanger bag from the heating system of FIG. 7.
Figure 9:
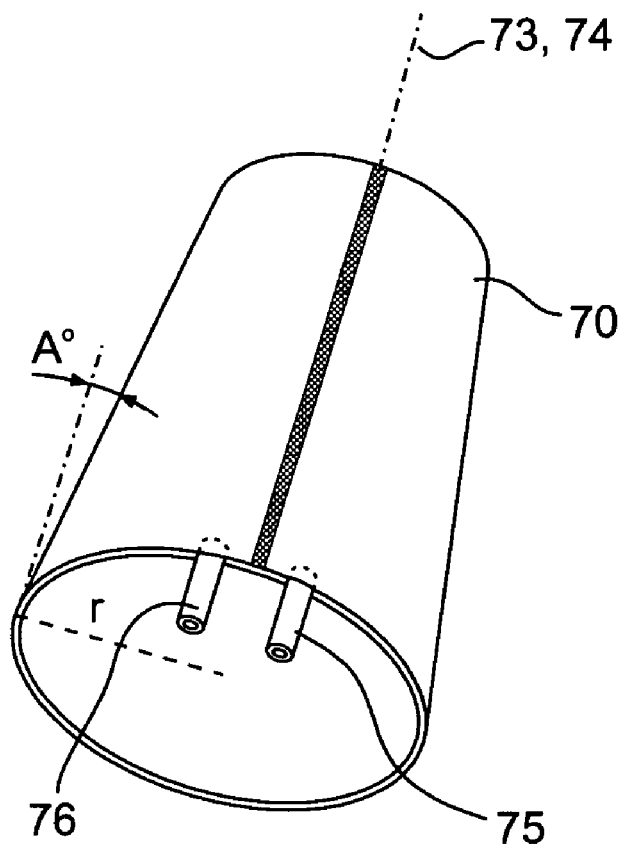
FIG. 9 is a rolled up view of the heat exchanger bag of FIG. 8.

Reference is now made to FIGS. 8–14, which illustrate a fluid heating system 54 or 64 from heating device 80, in accordance with a preferred embodiment of the present invention. In FIGS. 8–10, fluid heating system 54 or 64 includes a heating element 84 and a heat exchanger bag 70 for placement over heating element 84. In a preferred embodiment, heating element 84 is cone-shaped. Heating element 84 can alternatively be pyramidal or any other shape which is symmetrical along one axis and asymmetrical along a perpendicular axis. In another embodiment, heating element 84 is cylindrical.

FIG. 8 illustrates heat exchanger bag 70 in a flat configuration. By using a bag for heat exchange, a greater area is available for heat dissipation, resulting in smaller temperature gradients that do not harm the medications included within the fluid. In its flat configuration, heat exchanger bag 70 can be defined as a partial sector of a circle, with a central arc B and a radius L having edges 73, 74 and inlet/outlet tubes 75, 76. In a preferred embodiment, heat exchanger bag 70 is a bag or sack having therein a loop configuration of passageways 71 for fluid flow. As shown in FIG. 8, passageways 71 are constructed in a zigzag or "S" configuration, or any other suitable configuration for fluid 77 to pass through and either gain or release heat along the way. Fluid 77 flows into and out of heat exchanger bag 70 through inlet/outlet tubes 75, 76. In use, heat exchanger bag 70 is folded into a cone shape with overlapping edges 73, 74, and welded along this line, as shown in FIG. 9. FIG. 9 shows the folded cone-shaped heat exchanger bag 70 and FIG. 11 shows heat exchanger bag 70 after placement on a heating element 84. Heat exchanger bag 70 may be made from polyurethane, PVC, or any other suitable material.

An advantage to having a cone-shaped heating element 84 and a cone-shaped heat exchanger bag 70, is that heat exchanger bag 70 can be easily placed on heating element 84, after which a close fit is obtained, thereby providing even heating of the fluid flowing within heat exchanger bag 70. In order to provide this self-holding taper, a vertical angle A of the cone should preferably be between 1 and 4 degrees. In an exemplary preferred embodiment, the vertical angle A is 2 degrees. In order to obtain an angle A, heat exchanger bag 70 must be constructed of a particular circle sector with circle radius L and arc B. The radius of the base of the cone is r and the length of the cone is equal to the circle radius L. These parameters are related to each other as follows:

$r/L = \sin A.$

The length of arc B is $(B/360)*2\pi L$.

Thus, $(B/360)*2\pi L = 2\pi r$ (which is the circumference of the cone base)

$B = 360(r/L) = 360 \sin A.$

Thus, for A=2 degrees, B=12.56 degrees.

Heat exchanger bag 70 in its flat configuration, as shown in FIG. 8, can be defined as a modified sector, wherein the modification includes removal of an upper portion of the sector. However, all parameters remain as described above.

Reference is now made to FIGS. 10–13, which are illustrations of heating element 84, heating element 84 with heat exchanger bag 70 placed thereon, and heating element 84 with heat exchanger bag 70, a cover 90, and cover 90 placed on top of heat exchanger bag 70, respectively. Heating element 84 is designed so as to accept heat exchanger bag 70 placed thereon. In a preferred embodiment, heating element 84 has a structural element on a portion of it, such as a beveled top, for providing a close fit to cover 90 and thereby trapping air in heat exchanger bag 70, as will be described in further detail hereinbelow. As shown in FIG. 10, heating element 84 is usually made of aluminum and has therein one typical cartridge heater 85 such as FIREROD cartridge code number G4A54 from Watlow (St. Louis, Mo., USA) and a heating element temperature sensor 86. As shown in FIG. 11, heat exchanger bag 70 fits closely on top of heating element 84.

Once heat exchanger bag 70 is placed onto heating element 84, fluid 77 is introduced into system 100 via filling ports 55, 65. As fluid 77 is circulated through system 100, air rises to the top of heat exchanger bag 70. Cover 90, shown in FIG. 12, is then placed on top of heat exchanger bag 70, locking in the trapped air so as to allow fluid 77 to be substantially free of unwanted air, as shown in FIGS. 13 and 14.

Figures 13, 14:
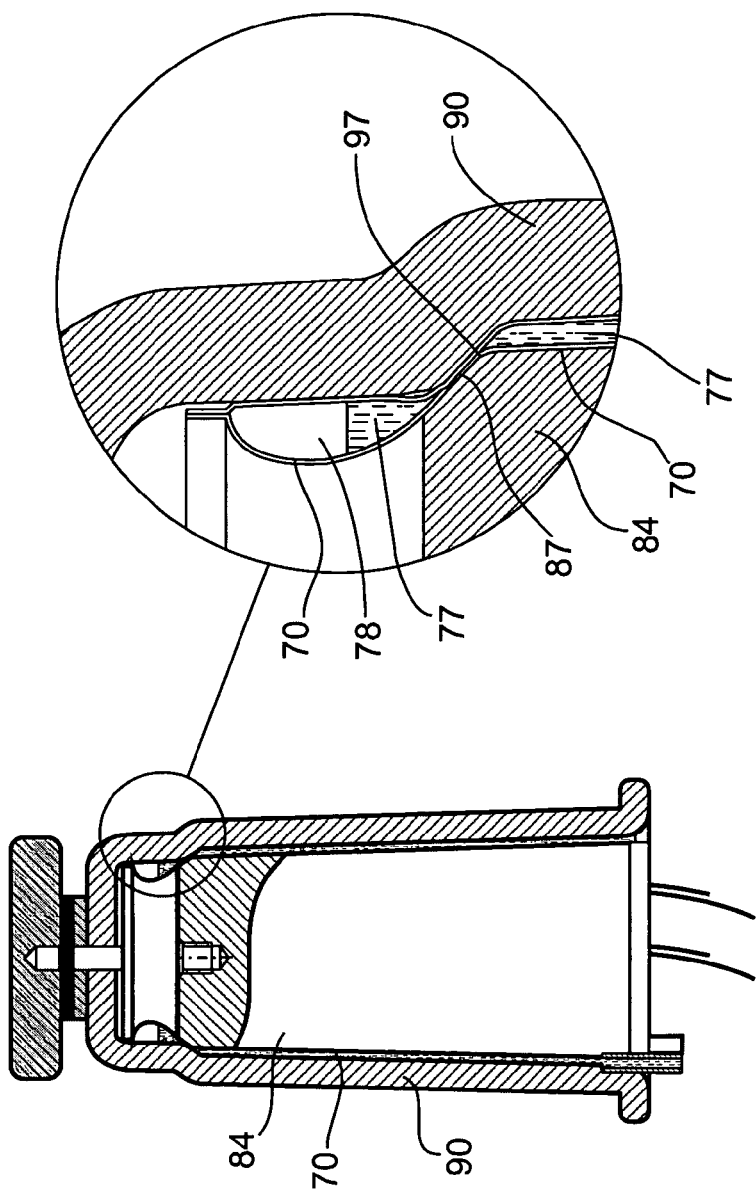
FIG. 13 is a partial cross-section of the cover of FIG. 12 placed on top of the heat exchanger bag and heating element combination of FIG. 11.
FIG. 14 is a close-up view of a portion of the combination shown in FIG. 13.

Reference is now made to FIGS. 13 and 14, which illustrate fluid heating system 54, 64 in greater detail. In a preferred embodiment, heating element 84 is cone shaped and has a bevel 87, and cover 90 is cone-shaped, and has a bevel 97 configuration to match bevel 87 of heating element 84. The bevel of cover 90 is at an angle with respect to the rest of the outer portion of cover 90 and of heating element 84. In one embodiment, the angle is between 20 and 70 degrees. In a preferred embodiment, the angle is approximately 45 degrees, as shown in FIGS. 13 and 14. Heat exchanger bag 70 is sandwiched between heating element 84 and cover 90. The size of the gap between heating element 84 and cover 90 determines the thickness of the stream of fluid 77 within heat exchanger bag 70. A goal is to minimize this thickness, so that fluid 77 is more evenly heated. In a preferred embodiment, the thickness is 1–3 millimeters. By providing a bevel at an angle, the size of the gap is set at a certain amount. Additionally, after initial fluid circulation in the priming stage, cover 90 is lowered down until bevel 97 of cover 90 meets bevel 87 of heating element 84, thus causing the bevel to choke the upper portion of heat exchanger bag 70, thereby trapping any air 78 found therein so that the fluid flow is free of unwanted air as it circulates through the system 100. Furthermore, without the additional compressible component of air, the pressure of fluid 77 can be manipulated more accurately.

A method for treatment of urinary tract disorders using the described device can include various therapeutic regimes, as will be described in further detail hereinbelow. The device of the present invention is designed so as to enable simultaneous treatment of a urinary bladder and an adjacent organ, such as the urethra. In addition, various combinations of heat, pressure and medication may be used in both the bladder and the urethra, either individually or in combination.

In one embodiment of the present invention, both the urinary bladder and the urethra are simultaneously heated, by heating the fluid flowing in and out of the corresponding lumens. In a further embodiment, medication may be added to the heated fluid. Examples of medications include, but are not limited to cytotoxic drugs such as mitomycin C or anti-inflammatory drugs such as heparin, or nerve desensitizing drugs such as resiniferatoxin. In yet a further embodiment, a pressure may be increased through filling ports 55, 65. The pressure may be a single continuous pressure, or alternatively, there may be several alternating pressures. Either of these types of pressures can be added to heated fluid with or without medication.

In other embodiments, the urinary bladder and the urethra are heated sequentially without changing catheter 12, which serves to ease treatment to the patient. The same possible combinations of heat, pressure, alternating pressure, and medication, can be used for each organ separately.

By combining heat treatment of the urinary bladder with heat treatment of the urethra, the effective heat generated in the area is improved without damaging surrounding tissue through the use of too high temperature as in thermotherapy. Specifically with respect to CPPS, interstitial cystitis, and TCC, generalized heating of the area may contribute to longer lasting effects of treatment. For illnesses which have unclear etiologies, such as CPPS and interstitial cystitis as well as detrusor-sphincter dyssynergia, simultaneous or sequential heating can aid in treatment by providing heat to several organs, allowing for the possibilities that either the urinary bladder or the urethra or both are problematic areas. Each of these treatments can be further adjusted according to need, based on temperature, pressure and medication. Thus, the methods described herein provide a broader range of treatments over a larger area with potentially longer lasting effects.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A system for treating urinary tract disorders comprising:
   (a) a catheter including:
      (i) a catheter body being sized and configured such that when placed within the urinary tract of an individual a proximal portion of said catheter body is adapted to resides outside the body of the individual, a middle portion of said catheter body is adapted to resides within a urethra of the individual and a distal portion of said catheter body is adapted to resides within a urinary bladder of the individual;

(ii) a fluid reservoir being attached to said catheter body at said middle portion of said catheter body;

(iii) a first conduit including at least one lumen, said first conduit being for communicating reservoir fluid from a first source outside the body through said proximal portion of said catheter body to said fluid reservoir;

(iv) a second conduit including at least one lumen, said second conduit being for communicating bladder fluid from a second source outside the body through said catheter body and into said urinary bladder; and (b) an extracorporeal unit including said first and said second sources of fluid and a heating device for heating fluid provided by said first and said second sources, said extracorporeal unit being in fluid communication with said first and said second conduits of said catheter.

2. The system of claim 1, wherein said first conduit includes two lumens, a first lumen being for communicating said reservoir fluid from said first source outside the body through said proximal portion of said catheter body to said fluid reservoir and a second lumen being for communicating said reservoir fluid from said fluid reservoir to said first source outside the body thereby enabling circulating of reservoir fluid between said first source and said fluid reservoir.

3. The system of claim 1, wherein said second conduit includes two lumens, a first lumen being for communicating said bladder fluid from said second source outside the body through said proximal portion of said catheter body to said urinary bladder and a second lumen being for communicating said bladder fluid from said urinary bladder to said second source outside the body thereby enabling circulating of bladder fluid between said second source and said urinary bladder.

4. The system of claim 1, wherein said fluid reservoir is selected from the group consisting of a bladder, an inflatable balloon, and a semi-permeable membrane.

5. The system of claim 1, wherein said first source and said second source are the same source.

6. The system of claim 1, wherein said reservoir fluid and said bladder fluid are the same fluid.

7. The system of claim 1, wherein the system further comprises at least one energy source being disposed within said fluid reservoir or on said distal portion of said catheter body.

8. The system of claim 7, wherein said at least one energy source and said catheter body are configured so as to enable energizing of said at least one energy source from outside the body when the catheter is positioned within the urinary tract of the individual.

9. The system of claim 7, wherein said energy source is configured to produce heat for heating fluid provided by said first and said second sources.

10. The system of claim 1, wherein said reservoir fluid is selected from the group consisting of gas, liquid, saline, water and medicated solution.

11. The system of claim 1, wherein said bladder fluid is selected from the group consisting of gas, liquid, saline, water and medicated solution.

12. The system of claim 1, wherein the catheter further comprises a fluid port hub being attached to a proximal end of said catheter body.

13. The system of claim 12, wherein said fluid port hub includes at least one temperature sensor being for sensing a temperature of said fluid.

14. The system of claim 1, wherein the catheter further comprises an anchor being attached to said distal portion of said catheter body.

15. The system of claim 14, wherein said anchor is a balloon anchor.

16. The system of claim 1, wherein the heating device comprises a power source, a cone shaped heating element and a controller, said controller being for controlling an amount of power delivered from said power source to said cone-shaped heating element, thereby controlling an amount of heat produced by said cone-shaped heating element.

* * * * *